United States Patent [19]

Grollier

[11] Patent Number: 4,477,375
[45] Date of Patent: Oct. 16, 1984

[54] CLEANING PRODUCT FOR THE HAIR AND SKIN, BASED ON ACYLISETHIONATES AND CATIONIC POLYMERS

[75] Inventor: Jean F. Grollier, Paris, France

[73] Assignee: L'OREAL, Paris, France

[21] Appl. No.: 461,524

[22] Filed: Jan. 27, 1983

[30] Foreign Application Priority Data

Jan. 29, 1982 [LU] Luxembourg .......................... 83911

[51] Int. Cl.$^3$ .................. C11D 1/12; C11D 1/65; C11D 1/62; A61K 7/06
[52] U.S. Cl. .................................. 252/542; 252/544; 252/545; 252/547; 252/DIG. 2; 252/DIG. 5; 252/DIG. 13; 424/70; 424/71
[58] Field of Search .............. 252/DIG. 2, DIG. 13, 252/DIG. 5, 557, 542, 545, 544, 547; 424/70, 71

[56] References Cited

U.S. PATENT DOCUMENTS

| | | | |
|---|---|---|---|
| 2,894,912 | 7/1959 | Geltz | 252/557 |
| 3,472,840 | 10/1969 | Stone et al. | 260/231 |
| 3,549,542 | 12/1970 | Holderby | 252/DIG. 13 X |
| 3,928,224 | 12/1975 | Vanlerberghe et al. | 252/172 |
| 3,957,970 | 5/1976 | Korkis | 252/DIG. 2 |
| 4,231,903 | 11/1980 | Lindermann et al. | 252/545 |
| 4,265,782 | 5/1981 | Armstrong et al. | 252/174.16 |
| 4,273,760 | 6/1981 | Koehler et al. | 424/70 |
| 4,307,079 | 12/1981 | Zorayan et al. | 424/70 |
| 4,381,259 | 4/1983 | Homma et al. | 252/DIG. 2 X |

FOREIGN PATENT DOCUMENTS

1155712 6/1969 United Kingdom .
1347051 2/1974 United Kingdom .

OTHER PUBLICATIONS

Seifen-Ole-Fette-Wasche, vol. 99, No. 12, Jun. 1, 1973, pp. 333–337.
Hanbuch der Kosmetika and Reichstoffe, 3rd ed., vol. 1, 1978, pp. 348, 349, 474.
CTFA Cosmetic Dictionary, 3rd ed., 1982, p. 245.

*Primary Examiner*—John E. Kittle
*Assistant Examiner*—Mukund J. Shah
*Attorney, Agent, or Firm*—Cushman, Darby & Cushman

[57] ABSTRACT

A cleaning composition suitable for the hair and/or skin, which comprises a cosmetically acceptable medium containing (a) at least one surface-active agent of the formula:

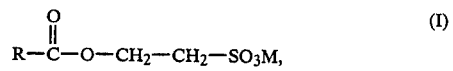

in which R denotes a linear or branched alkyl group and M denotes an alkali metal or alkaline earth metal or an amine, and (b) at least one cationic polymer selected from (i) cellulose ether derivatives containing quaternary ammonium groups, (ii) cyclic polymers containing, as the main constituent of the chain, units corresponding to the formula (III), or (III')

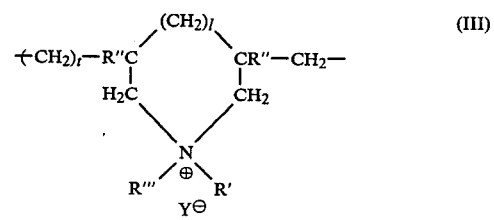

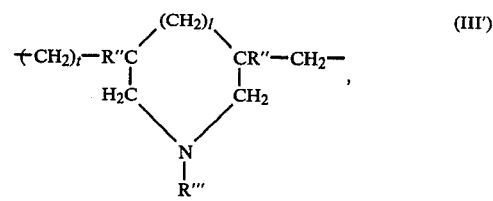

in which l and t are 0 or 1 and l+t=1, R" denotes hydrogen or methyl, R'" and R' independently of one another denote an alkyl group having 1 to 22 carbon atoms, a hydroxyalkyl group or a lower amidoalkyl group or R'" and R', together with the nitrogen atom to which they are attached, denote a heterocyclic group and Y⁻ denotes an anion, and (iii) copolymers containing said units of the formula (II) or (II') and units derived from acrylamide or from diacetoneacrylamide.

15 Claims, No Drawings

CLEANING PRODUCT FOR THE HAIR AND SKIN, BASED ON ACYLISETHIONATES AND CATIONIC POLYMERS

The present invention relates to cleaning products for the hair and/or skin, based on acylisethionates and certain cationic polymers, and also to the process in which these compositions are used.

For many years, cleaning products for the hair and/or skin have been formulated from surface-active agents which can be anionic, amphoteric, non-ionic or cationic and which are used by themselves or in a mixture. The overall use concentration is generally between 5 and 20%.

Furthermore, it has already been recommended, with a view to improving the cosmetic properties of these compositions, to add cationic compounds, and in particular cationic polymers, thereto.

As is known, cationic polymers improve the softness by depositing on the hair, and the hair is the easier to comb out, the greater the amount of polymers deposited. This deposit is the larger, the more sensitised the fibre, that is to say the greater the number of sulphonic groups it contains which are capable of fixing the cationic charges of the polymer.

We have found that the deposits of these polymers are substantially larger if non-ionic media rather than anionic media are used. This difference in efficacy is partly due to the interactions between the cationic polymer and the anionic surface-active agent, which partially inhibits the deposition of polymer.

However, anionic surface-active agents have better detergency properties than non-ionic surface-active agents, so that it has seemed desirable to be able to retain these properties while at the same time improving the softness of the hair and/or skin to the touch and the comb-out of the hair.

We have found, in particular, that the interaction between the cationic polymer and the anionic surface-active agent is particularly strong for surface-active agents of high polarity and in particular for sulphated or sulphonated anionic surface-active agents.

It has now been discovered that, by using acylisethionates as surface-active agents, a substantially improved deposition of certain cationic polymers is obtained, which is particularly surprising in view of the fact that acylisethionates contain a sulphonic group having, a priori, an interaction capable of inhibiting the deposition of the cationic polymer on the skin or hair.

The invention thus relates to a cleaning composition for the hair and/or skin, based on acylisethionates and certain cationic polymers.

The invention also relates to a process for cleaning the hair and skin, which essentially uses a composition of this type.

Further objects of the invention will become apparent on reading the description and the examples which follow.

The cleaning composition for the hair and/or skin, according to the invention, comprises, in combination, in a cosmetically acceptable medium, at least one surface-active agent of the formula:

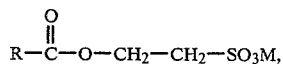

(I)

in which R denotes a linear or branched alkyl group and M denotes an alkali metal or alkaline earth metal or an amine, and at least one cationic polymer chosen from amongst (1) Cellulose ether derivatives containing quaternary ammonium groups and corresponding to the structural formula:

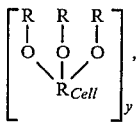

(1)

in which $R_{Cell}$ is the residue of an anhydroglucose unit, Y is a number having a value of about 50 to about 20,000 and each R individually represents a substituent which is a group of the general formula:

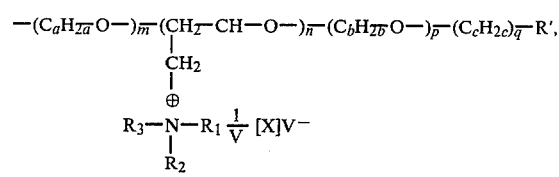

in which a is an integer having a value of 2 or 3; b is an integer having a value of 2 or 3; c is an integer having a value of 1 to 3; m is an integer having a value of 0 to 10; n is an integer having a value of 0 to 3; p is an integer having a value of 0 to 10; q is an integer having a value of 0 or 1; R' is a radical of the formula:

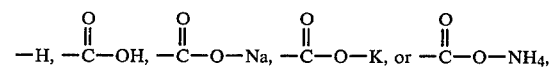

it being clearly understood that if q is equal to zero, R' represents —H; $R_1$, $R_2$ and $R_3$, taken individually, each represent an alkyl, aryl, aralkyl, alkaryl, cycloalkyl, alkoxyalkyl or alkoxyaryl radical, it being possible for each of the radicals $R_1$, $R_2$ and $R_3$ to contain up to 10 carbon atoms, it being clearly understood that in the case of an alkoxyalkyl radical, there are at least 2 carbon atoms separating the oxygen atom from the nitrogen atom, and it also being clearly understood that the total number of carbon atoms present in the radicals represented by $R_1$, $R_2$ and $R_3$ is between 3 and 12, or $R_1$, $R_2$ and $R_3$, taken together, can represent, with the nitrogen atom to which they are attached, one of the following radicals: pyridine, α-methylpyridine, 3,5-dimethylpyridine, 2,4,6-trimethylpyridine, N-methylpiperidine, N-ethylpiperidine, N-methylmorpholine or N-ethylmorpholine; X is an anion; V is an integer equal to the valency of X; the average value of n per anhydroglucose unit of this cellulose ether is between 0.01 and about 1; and the average value of (m+n+p+q) per anhydroglucose unit of this cellulose ether is between about 0.01 and about 4.

The polymers which are more particularly preferred are those corresponding to the above formula (I) in which a and b are equal to 2, g is equal to 0, m, n and p having the abovementioned values, R' denotes hydrogen and $R_1$, $R_2$ and $R_3$ denote methyl. The average values per anhydroglucose unit are 0.35 to 0.45 for n and 1 to 2 for the sum of m+p, and X denotes chloride.

The preferred ethers according to the invention have viscosities of 50 to 35,000 centipoises at 25° C., in 2% strength by weight aqueous solutions, measured by ASTM method D-2364-65 (Brookfield viscometer, LVF model, 30 rpm, No. 2 spindle), and the ethers which are particularly preferred are those produced by the firm Union Carbide Corporation under the trademarks "JR-125", "JR-400" and "JR-30M", which respectively denote a polymer of the type described above having a viscosity equal to 125 centipoises, 400 centipoises and 30,000 centipoises, and those sold under the name LR, such as LR 400 and LR 30M.

These polymers are described in French Pat. No. 1,492,597.

(2) Cyclic polymers having a molecular weight of 20,000 to 3,000,000, such as homopolymers containing, as the main constituent of the chain, units corresponding to the formula (III) or (III'):

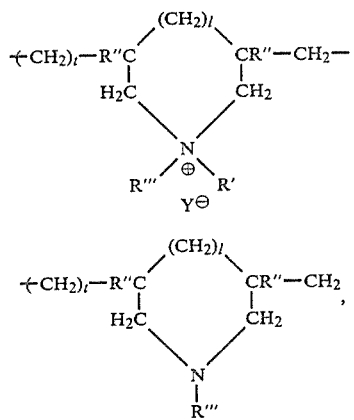

in which l and t are equal to 0 or 1 and the sum of $l+t=1$, R" denotes hydrogen or methyl and R''' and R' independently of one another denote an alkyl group having from 1 to 22 carbon atoms, a hydroxyalkyl group in which the alkyl group preferably has 1 to 5 carbon atoms, or a lower amidoalkyl group, and R''' and R' can denote, together with the nitrogen atom to which they are attached, heterocyclic groups such as piperidinyl or morpholinyl, and also copolymers containing units of the formula III or III' and units derived from acrylamide or from diacetone-acrylamide; $y^\ominus$ is an anion such as bromide, chloride, acetate, borate, citrate, tartrate, bisulphate, bisulphite, sulphate or phosphate.

Amongst the quaternary ammonium polymers of the type defined above, there may be mentioned the dimethyldiallylammonium chloride/acrylamide copolymer having a molecular weight of more than 500,000 and sold under the name MERQUAT 550 by MERCK.

These polymers are described in French Pat. No. 2,080,759 and its Certificate of Addition No. 2,190,406.

In the abovementioned formula (I), R preferably denotes an alkyl group having between 8 and 18 carbon atoms; the groups which are particularly preferred consist of a group having 12 to 14 carbon atoms or a group derived from copra oil. M preferably denotes sodium, potassium or magnesium, sodium being particularly preferred.

A particularly preferred embodiment of the invention is a composition containing the acylisethionate of the formula (I) described above, in combination with cellulose ether derivatives containing quaternary ammonium groups, and in particular the product sold under the name JR 400 by Union Carbide and the cyclic polymer having a molecular weight of more than 500,000 and sold under the name MERQUAT 550 by MERCK.

The surface-active agent and the cationic polymer are present in a cosmetically acceptable medium, which can be liquid or solid.

The cationic polymers used according to the invention are preferably included in proportions of 0.05 to 5% by weight, relative to the total weight of the composition, and the surface-active agent of the formula (I) is preferably used in proportions of 5 to 30% by weight and in particular of 5 to 15% for the liquid forms, it being possible for the proportions to range up to 90% for the solid forms.

The preferred ratio of the cationic polymer, expressed as active ingredient, to the surface-active agent of the formula (I) is between 0.01 and 0.3.

If the compositions are intended to be used for cleaning the skin, they can be presented in the form of a cleansing cream, a milk, a gel, a make-up remover lotion or a thickened lotion. If the compositions are intended for washing the hair, they can be presented in the form of a shampoo, or a rinse-off treating product to be applied before or after shampooing or before or after other hair treatments.

If the compositions are in liquid form, they can contain water, a cosmetically acceptable solvent such as a monoalcohol, a polyalcohol, a glycol ether or their esters, and also mixtures thereof.

These compositions can contain various cosmetic adjuvants such as perfumes, dyestuffs, preservatives, sequestering agents, thickeners, antioxidants, sun filters and foam stabilisers, and also any other adjuvant chosen according to the application envisaged. The pH of the compositions can be between 5 and 8.5.

The compositions which are more particularly preferred are the liquid compositions, and they have a pH substantially in the region of neutrality and preferably of between 6 and 8.

An advantageous embodiment of the invention consists in introducing thickeners into the compositions according to the invention, these thickeners making it possible to obtain a good viscosity and to keep the surface-active agent of the formula (I) in suspension in an unctuous form. The thickeners can be chosen, in particular, from amongst vegetable thickeners such as gum arabic, karaya gum, gum tragacanth, guar gum, carob gum, tara gum, pectins, alginates, carragheenates and agar-agar; cellulose derivatives such as methylcellulose, hydroxymethylcellulose, hydroxyethylcellulose, hydroxypropylcellulose and hydroxypropylmethylcellulose; synthetic polymers such as sodium polyacrylate, polyvinyl alcohol and carboxylic polymers derived from acrylic acid, such as carbopols; and polyethylene glycol esters and polyethylene glycol ethers.

These compositions can also contain other surface-active agents such as, for example, salts of fatty acid/polypeptide condensates, and there may be mentioned, in particular, the triethanolamine salts of a lauric acid/keratin polypeptide condensate and the potassium salts of a coconut fatty acid/collagen polypeptide condensate, sold under the name LAMEPON S by GRUNAU.

These compositions can also contain non-ionic surface-active agents, used by themselves or in a mixture; the following may be mentioned in particular: polyoxyethyleneated, polyoxypropyleneated or polyglycerolated alcohols, alkylphenols and fatty acids having a linear fatty chain containing 8 to 18 carbon atoms and most frequently containing 2 to 30 mols of ethylene oxide. There may also be mentioned ethylene oxide/propylene oxide copolymers, condensates of ethylene oxide and propylene oxide with fatty alcohols, polyoxyethyleneated fatty amides, polyoxyethyleneated fatty amines, ethanolamides, fatty acid esters of glycol, oxyethyleneated or non-oxyethyleneated fatty acid esters of sorbitan, fatty acid esters of sucrose, fatty acid esters of polyethylene glycols, phosphoric acid triesters and fatty acid esters of glucose derivatives.

Other compounds included in this class are: products resulting from the condensation of a monoalcohol, an α-diol, an alkylphenol, an amide or a diglycolamide with glycidol, such as:

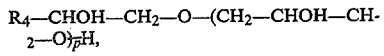

$R_4$—CHOH—CH$_2$—O—(CH$_2$—CHOH—CH$_2$—O)$_p$H, in which $R_4$ denotes an aliphatic, cycloaliphatic or arylaliphatic radical preferably having between 7 and 21 carbon atoms, and mixtures thereof, it being possible for the aliphatic chains to contain ether, thioether or hydroxymethylene groups, and in which p is between 1 and 10 inclusive, such as the products described in French Pat. No. 2,091,516;

compounds corresponding to the formula:

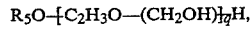

$R_5O$—[$C_2H_3O$—($CH_2OH$)$_q$]$_q$H, in which $R_5$ denotes an alkyl, alkenyl or alkylaryl radical and q has a statistical value of between 1 and 10 inclusive, such as the compounds described in French Pat. No. 1,477,048;
and
compounds corresponding to the formula:

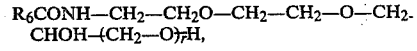

$R_6$CONH—CH$_2$—CH$_2$O—CH$_2$—CH$_2$—O—CH$_2$—CHOH—(CH$_2$—O)$_r$H, in which $R_6$ denotes a linear or branched, saturated or unsaturated aliphatic radical, or a mixture of such radicals, which can optionally contain one or more hydroxyl groups, which has between 8 and 30 carbon atoms and which is of natural or synthetic origin, and r represents an integer or decimal number from 1 to 5 and denotes the average degree of condensation, such as the compounds described in French Pat. No. 2,328,763.

Amphoteric surface-active agents can also be used, and there may be mentioned, more particularly, alkylamino-monopropionates and -dipropionates, betaines such as N-alkylbetaines, N-alkylsulphobetaines and N-alkylamidobetaines, cycloimidinium compounds such as alkylimidazolines, and asparagine derivatives.

If the compositions are in solid form, they contain, in addition to the surface-active agent of the formula (I) and the cationic polymer, thickeners other than polyethylene glycol ethers, superfatting agents such as lecithin, binders such as polyethylene glycols, plasticisers, foam stabilisers, sequestering agents or antioxidants.

The process for cleaning the hair and skin, according to the invention, consists essentially in applying a composition such as described above to the wet hair and/or wet skin, and, after application and an interval of a few minutes, in rinsing with water.

The combination according to the present invention can also be formed on the hair or skin by applying the acylisethionate of the formula (I) in a first step and the cationic polymer in a second step, by means of compositions corresponding to the above definitions.

The examples which follow illustrate the invention.

EXAMPLE 1

| FENOPON AC 78 | 10 g |
| --- | --- |
| MERQUAT 550 | 1 g of active ingredient |
| Water q.s. | 100 g |
| pH 7 | |

The hair is washed with this composition; after drying, the hair is soft to the touch and easy to comb out.

EXAMPLE 2

| FENOPON AC 78 | 15 g |
| --- | --- |
| JR 400 | 0.5 g of active ingredient |
| Water q.s. | 100 g |
| pH 6 | |

This composition is used to wash the hands or body. After rinsing, the skin is soft.

In Examples 1 or 2, the FENOPON AC 78 can be replaced by HOSTAPON KA (sodium coconut-isethionate) sold by HOECHST.

The surprising effect of the improvement in the deposition of the cationic polymer was observed by means of the following experiment:

Compositions are prepared which contain 1%, in terms of active ingredient, of various cationic polymers in the surface-active agents taken to contain 10% of active ingredient, and which are at pH 7.

A control composition, which contains only the surface-active agent and which is at pH 7, is prepared in parallel.

1 g swatches of bleached hair are immersed in 2.5 g of the various compositions for 15 minutes at ambient temperature.

The swatches are then rinsed in running water.

The deposit of cationic polymer on the hair is then demonstrated with the aid of the following colorimetric test: the treated swatches are immersed in 10 ml of an aqueous solution of the acid dyestuff SIRIUS ROT F3B from BAYER, obtained by fivefold dilution of the following preparation:

0.4665 g of dyestuff
0.1250 g of glacial acetic acid
q.s. 100 g of water.

After a contact time of 1 minute at ambient temperature, the swatches are rinsed five times in 50 ml of softened water.

The swatch is the more strongly coloured, the larger the deposit of cationic polymer.

The deposition of several polymers was compared using, as the reference surface-active agent, the sodium salt of a sulphated alkanol oxyethyleneated with 2.2 mols of ethylene oxide. 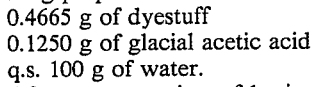 This surface-active agent was compared with the surface-active agent according to the invention.

It is shown that the deposit of cationic polymer is much larger in the presence of the surface-active agent according to the invention than in the presence of the sulphated oxyethyleneated alkanol. This fact was observed in particular with the compositions described in the foregoing examples.

In the foregoing examples, the commercial products represent the following compounds:

| | |
|---|---|
| FENOPON AC 78 | sodium acylisethionate (acyl is a hydrocarbon residue of copra fatty acids), sold by GAF. |
| MERQUAT 550 | Dimethyldiallyammonium chloride/acrylamide copolymer of molecular weight 500,000, sold by MERCK. |
| JR 400 | Polymer resulting from the reaction of hydroxyethylcellulose with epichlorohydrin, quaternised with trimethylamine, sold by UNION CARBIDE. |

We claim:

1. A cleaning composition for the hair and skin consisting essentially of, in combination, in a cosmetically acceptable medium, (a) at least one surface-active agent of the formula:

$$R-\overset{O}{\underset{\|}{C}}-O-CH_2-CH_2-SO_3M$$

wherein R denotes a linear or branched alkyl group and M denotes on alkali metal or alkaline earth metal or an amine, and (b) at least one cationic polymer selected from
 (i) cellulose ether derivatives containing quaternary ammonium groups,
 (ii) cyclic polymers containing, as the main constituent of the chain, units corresponding to the formula (III) or (III'):

$$-(CH_2)_t-R''C\underset{H_2C}{\overset{(CH_2)_l}{\diagup}}\underset{CH_2}{\overset{CR''-CH_2-}{\diagdown}}\underset{\underset{Y^\ominus}{R'''\diagup\overset{\oplus}{N}\diagdown R'}}{} \quad (III)$$

$$-(CH_2)_t-R''C\underset{H_2C}{\overset{(CH_2)_l}{\diagup}}\underset{CH_2}{\overset{CR''-CH_2-}{\diagdown}}\underset{\underset{R'''}{N}}{} \quad (III')$$

wherein l and t are 0 or 1 and 1+t=1, R" denotes hydrogen or methyl, R''' and R' independently of one another denote an alkyl group having 1 to 22 carbon atoms, a hydroxyalkyl group or a lower amidoalkyl group or R''' and R' together with the nitrogen atom to which they are attached, denote a heterocyclic group and $Y^\ominus$ denotes an anion, and
 (iii) copolymers containing said units of the formula (III) or (III') and units derived from acrylamide or from diacetoneacrylamide.

2. A composition according to claim 1 wherein R denotes an alkyl group having from 8 to 18 carbon atoms.

3. A composition according to claim 2 wherein R is selected from an alkyl group having 12 to 14 carbon atoms or a group derived from copra oil.

4. A composition according to claim 1 wherein M is selected from sodium, potassium or magnesium.

5. A composition according to claim 1 wherein one or both of R''' and R' is a hydroxyalkyl group in which the alkyl group has from 1 to 5 carbon atoms or a lower amidoalkyl group of from 1 to 5 carbon atoms or R''' and R', together with the nitrogen atom to which they are attached, denote a piperidinyl or morpholinyl group.

6. A composition according to claim 1 wherein $Y^-$ is an anion selected from bromide, chloride, acetate, borate, citrate, tartrate, bisulphate, bisulphite, sulphate or phosphate.

7. A composition according to claim 1 wherein the cationic polymer (b) is present in proportions of 0.05 to 5% by weight, relative to the total weight of the composition.

8. A composition according to claim 1 wherein the surface-active agent (a) is present in an amount of 5 to 30% by weight for a composition in liquid form and in an amount of up to 90% by weight for a composition in solid form.

9. A composition according to claim 1 wherein the ratio of the cationic polymer (b) to the surface-active agent (a) is from 0.01 and 0.3:1.

10. A composition according to claim 1 wherein the composition is liquid and the cosmetically acceptable medium is selected from water, a solvent or a mixture thereof.

11. A composition according to claim 1 which contains a thickener selected from vegetable thickeners, cellulose derivatives, synthetic polymers other than cationic polymers, polyethylene glycol esters or polyethylene glycol ethers.

12. A composition according to claim 1 which is in the form of a liquid and contains from 5 to 15% by weight of the surface-active agent (a).

13. A composition, suitable for cleaning the skin, according to claim 1 which selected from a cleansing cream, a milk, a gel, a make-up remover lotion or a thickened lotion.

14. A composition, suitable for washing the hair, according to claim 1 which is selected from a shampoo or a rinse-off product applied before or after shampooing.

15. A process for cleaning the hair or skin, which process comprises applying to the hair or skin at least one composition as claimed in claim 1.

* * * * *